US005455035A

United States Patent [19]
Guerrero et al.

[11] Patent Number: 5,455,035
[45] Date of Patent: Oct. 3, 1995

[54] CLEAR TWO-PHASE COSMETIC COMPOSITION

[75] Inventors: Angel A. Guerrero, Huntington; Anthony Vargas, Monroe; Alan J. Meyers, Trumbull, all of Conn.

[73] Assignee: Elizabeth Arden Company, Division of Conopco, Inc., New York, N.Y.

[21] Appl. No.: 181,268

[22] Filed: Jan. 13, 1994

[51] Int. Cl.$^6$ .................................................. A61K 7/00
[52] U.S. Cl. ........................... 424/401; 424/60; 514/558; 514/560
[58] Field of Search .............................. 421/401; 514/558, 514/560

[56] References Cited

U.S. PATENT DOCUMENTS

| | | | |
|---|---|---|---|
| 1,535,529 | 4/1925 | Hopkins | 424/49 |
| 1,699,532 | 1/1929 | Hopkins | 424/49 |
| 3,708,431 | 1/1973 | Prussin | 252/188.3 |
| 4,211,341 | 7/1980 | Weyn | 222/94 |
| 4,372,874 | 2/1983 | Modrovich | 436/176 |
| 4,487,757 | 12/1984 | Kiozpeoplou | 424/71 |
| 4,528,180 | 7/1985 | Schaeffer | 424/52 |
| 4,687,663 | 8/1987 | Schaeffer | 424/52 |
| 4,818,521 | 4/1989 | Tamabuchi | 424/62 |
| 4,839,161 | 6/1989 | Bowser et al. | 424/59 |
| 4,849,213 | 7/1989 | Schaeffer | 424/53 |
| 4,983,382 | 1/1991 | Willmott et al. | 424/62 |
| 5,078,989 | 1/1992 | Ando et al. | 424/62 |
| 5,137,723 | 8/1992 | Yamamoto et al. | 424/400 |
| 5,140,043 | 8/1992 | Darr et al. | 514/474 |

*Primary Examiner*—Jyothsna Venkat
*Attorney, Agent, or Firm*—Milton L. Honig

[57] ABSTRACT

A cosmetic product formed as a multi-compartment dispenser is provided wherein a first and second substance is stored apart from one another in separate compartments. The first substance incorporates a liquid organic acid in a pharmaceutically acceptable carrier. The second substance incorporates an alkaline agent present in an amount to neutralize the liquid organic acid to thereby form a surface active material.

4 Claims, No Drawings

CLEAR TWO-PHASE COSMETIC COMPOSITION

BACKGROUND OF THE INVENTION

1. Field of the Invention

The invention relates to a cosmetic product formed as a clear two-phase composition with surfactant activity.

2. The Related Art

A pair of copending application Ser. Nos. 08/181,273 and 08/181,274, both filed on Jan. 13, 1994 pending. Have described a two-phase composition for delivering ascorbic acid (Vitamin C). In the development of this two-phase product, it was found necessary to include a surfactant while maintaining clarity in both phases. A further problem concerned the anhydrous nature of the first of the phases that required a relatively low pH to maintain stability of the ascorbic acid against decomposition. The other phase was an aqueous system of relatively higher pH. Use of traditional surfactant salts in the aqueous phase resulted in problems with clarity. Incorporation of the surfactant, a relatively basic substance, into the anhydrous composition caused unacceptable conversion of the surfactant salt into an acid form.

Accordingly, it is an object of the present invention to provide a system that will deliver a surfactant from a dual-phase cosmetic product.

Another object of the present invention is to provide a system capable of delivering a surfactant from a dual-phase system in which both phases are transparent.

These and other objects of the present invention will become more readily apparent through the following summary, detailed discussion and Examples.

SUMMARY OF THE INVENTION

A cosmetic product is provided which is formed as a multi-compartment dispenser, wherein a first and second substance are stored apart from one another in separate compartments of the dispenser:

(i) the first substance comprising from 0.01 to 50% by weight thereof of a liquid organic acid and from 0.01 to 99% by weight thereof of a pharmaceutically acceptable carrier; and (ii) the second substance comprising an alkaline agent present in an effective amount to neutralize the liquid organic acid to thereby form a surfactant active material.

DETAILED DESCRIPTION OF THE INVENTION

Now it has been discovered that a surfactant active material can be stably stored in a transparent formula by compartmentally segregating an organic acid surfactant precursor from an alkaline neutralizing agent. Only upon expression of the acid and neutralizing agent from the respective two separate compartments will these materials blend together to provide upon neutralization the surface active material.

Accordingly, the present invention provides a cosmetic product in the form of a multi-compartment dispenser. A first and second substance will be stored in respective separate compartments of that dispenser. The first substance will include a liquid organic acid at a concentration from about 0.01 to about 50%, preferably from about 0.5 to about 25%, optimally between about 1 and 5% by weight of the first substance.

The term "liquid" according to this invention means an acid having a melting point no higher than 50° C., preferably no higher than 40° C., optimally no higher than 20° C.

Typical liquid organic acids include $C_{10}$–$C_{22}$ fatty acids, hydrocarbyl sulphonic acids, hydrocarbyl sulphuric acids, hydrocarbyl phosphoric acids and hydrocarbyl phosphonic acids. The term "hydrocarbyl" is defined as an organic $C_1$–$C_{40}$ moiety selected from the group consisting of alkyl, alkenyl, benzyl and aryl radicals which may be substituted or unsubstituted as well as branched or unbranched. There may also be alkoxylation between the hydrocarbyl and acid groups. Illustrative of organic acids are isostearic acid, oleic acid, linolenic acid, linoleic acid, palmitoleic acid, ricinoleic acid, oleyl isethionic acid, isostearyl isethionic acid, isostearyl sulphonic acid, monoisostearyl phosphoric acid, di(oleyl) phosphoric acid and 1-linoleyl sulphonic acid.

Another component of the first substance will be a pharmaceutically acceptable carrier ranging in concentration from about 0.1 to about 99%, preferably from about 25 to about 90%, optimally between about 70 and 85% by weight of first substance.

A wide variety of carriers can be utilized to deliver the liquid organic acid. The carrier may be water although preferably it will be an anhydrous vehicle. Particularly preferred are monohydric and/or polyhydric alcohols. Most preferred is polyethylene glycol of molecular weight between 200 and 1,000, preferably about 400.

Esters are another category of suitable carriers. Among esters that may be utilized are:

(1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are $C_{12}$–$C_{15}$ alcohol benzoate esters.

(2) Alkenyl esters of fatty acids having 10 to 20 carbon atoms. Examples thereof include oleyl myristate, oleyl stearate, and oleyl oleate.

(3) Ether-esters such as fatty acid esters of ethoxylated fatty alcohols.

(4) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) Sterols esters, of which cholesterol fatty acid esters are examples thereof.

Silicone oils may also be used as carriers. These oils may be either volatile or nonvolatile. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Examples of preferred volatile silicone oils useful herein include: Dow Corning 344, Dow Corning 345 and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The nonvolatile silicone oils useful in compositions of this invention are exemplified by the polyalkyl siloxanes, polyalklyaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Among the preferred nonvolatile silicones useful in the present compositions are the polydimethyl siloxanes having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol and cetyl dimethicone are especially preferred because these materials also function as emulsifiers and emollients.

Among other skin benefit agents there may be present ascorbic acid, especially when the substance is dissolved or suspended in an anhydrous composition. The amount of the ascorbic acid may range anywhere from about 0.001 to about 50% by weight of the first substance.

Acidifying agents may also be included in the composition of the first substance. These may be either organic or inorganic and range in an amount from about 0.1 to about 20%, preferably between about 1 and 10%, optimally between about 2 and 6% by weight. The acids may include alginic acid, citric acid, malic acid, succinic acid, lactic acid, glycolic acid, tartaric acid, sorbic acid, phosphoric acid, acid phosphate salt, acid pyrophosphate salt, bitartrate salt and metal acid citrate.

Thickeners or viscosifiers may be present in amounts up to about 10% by weight. As known to those skilled in the art, the precise amount of thickeners can vary depending upon the desired consistency and thickness of the composition. Exemplary thickeners are xanthan gum, sodium carboxymethyl cellulose, hydroxyalkyl and alkyl celluloses, and cross-linked acrylic acid polymers such as those sold by B.F. Goodrich under the Carbopol trademark. Most preferred is methyl cellulose and hydroxypropyl methyl cellulose at levels from 0.1 to 5%, preferably from about 0.2 to 1%, optimally about 0.5% by weight of the aqueous composition.

Preservatives can desirably be incorporated into the cosmetic compositions of this invention to protect against the growth of potentially harmful microorganisms. While it is in the aqueous phase that microorganisms tend to grow, microorganisms can also reside in the anhydrous or oil phase. As such, preservatives which have solubility in both water and oil are preferably employed in the present compositions. Suitable traditional preservatives for compositions of this invention are alkyl esters of parahydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methylparaben, imidazolidinyl urea, sodium dehydroacetate, propylparaben, trisodium ethylenediamine tetraacetate (EDTA) and benzyl alcohol. The preservative should be selected having regard for possible incompatibilities between the preservative and other ingredients. Preservatives are preferably employed in amounts ranging from about 0.01% to about 2% by weight of the composition.

Minor adjunct ingredients may also include fragrances, antifoam agents, opacifiers (e.g. titanium dioxide) and colorants, each in their effective amounts to accomplish their respective functions. Particularly useful minor ingredients are vitamin E linoleate, sodium hyaluronate and aloe vera gel, as well as other botanicals.

A sunscreen agent is a further desirable ingredient of the compositions of this invention. This ingredient is preferably incorporated into the anhydrous substance or oily phase. The term "sunscreen agent" as used herein defines ultraviolet ray-blocking compounds exhibiting absorption within the wavelength region between 290 and 400 nm. Sunscreens may be classified into five groups based upon their chemical structure: para-amino benzoates; salicylates; cinnamates; benzophenones; and miscellaneous chemicals including menthyl anthranilate and digalloyl trioleate. Inorganic sunscreens may also be used including titanium dioxide, zinc oxide, iron oxide and polymer particles such as those of polyethylene and polyamides. Preferred materials include p-aminobenzoic acid and its derivatives, anthranilates; salicylates; cinnamates; coumarin derivatives; azoles; and tannic acid and its derivatives.

According to the present invention there is also required a separate second substance which contains an alkaline agent present in an effective amount to neutralize the liquid organic acid to thereby form the surfactant active material. The alkaline agent may be present in an amount from about 0.5 to about 30%, preferably from about 1.5 to about 10%, optimally between about 2 and 5% by weight of the aqueous composition.

Alkaline agents may either be organic or inorganic having a pH below 7. Typical of the inorganic materials are sodium hydroxide and potassium hydroxide. However, the organic alkaline agents are preferred because they are less harsh to the skin. These include ammonia, alkylamines, hydroxyalkylamines and alkanolamines. Illustrative of these are triethylamine, triethanolamine, diethanolamine, tetra(hydroxypropyl) diamine, 2-amino-2-methylpropan-1-ol, 2-amino-2-ethyl-1,3-propanediol and 2-amino-2-hydroxymethyl-1,3-propanediol.

A pharmaceutically acceptable carrier will also be present in the second substance. This carrier may be anhydrous but is preferred to be aqueous. Thus, the aqueous composition may include a major amount of water ranging from about 40 to about 99%, preferably between 60 and 95%, optimally between 80 and 85% by weight of the second substance.

Additional or alternative carriers, as well as thickeners, preservatives and minor adjunct ingredients as described for incorporation into the first substance may also be utilized for the second substance.

According to the present invention there is required a multi-compartment dispenser. Illustrative of such dispensers are those disclosed in U.S. Pat. Nos. 1,639,699 and 1,699,532, each to Hopkins, describing double collapsible tubes. Separation of reactive components is also described in U.S. Pat. No. 4,211,341 (Weyn). Other examples are those found in U.S. Pat. No. 4,487,757 (Kiozpeoplou) in FIG. 1 as well as U.S. Pat. Nos. 4,528,180, 4,687,663 and 4,849,213, each of which is to Schaeffer.

For purposes of this invention, the weight ratio of the first to second composition may range from about 10:1 to 1:10, preferably 2:1 to 1:2, optimally about 1:1.

The following examples will more fully illustrate the embodiments of this invention. All parts, percentages and proportions referred to herein and in the appended claims are by weight unless otherwise indicated.

EXAMPLE 1

An aqueous and an anhydrous compositions were prepared according to the formulations set forth below. Each of the compositions were then charged to a respective separate compartment of a dual compartment dispensing apparatus. Each of the compositions include the following components:

|  | Wt. % |
|---|---|
| COMPOSITION A | |
| Aqueous Composition | |
| Deionized Water | 83.0 |
| Ethyl Alcohol | 7.5 |
| Butylene Glycol | 5.0 |
| Sodium Bicarbonate | 3.0 |
| Triethanolamine | 1.0 |
| Methocel 40-101 (hydroxypropylmethyl cellulose) | 0.5 |
| COMPOSITION B | |
| Anhydrous Composition | |
| Carbowax 400 (polyethylene glycol) | 84.0 |
| Ascorbic Acid (Vitamin C) | 5.0 |
| Ethyl Alcohol | 5.0 |
| Anhydrous Citric Acid | 3.0 |
| Isostearic Acid | 3.0 |

EXAMPLE 2

An aqueous and an anhydrous composition according to the present invention are set forth below. Each of the compositions is charged to a respective separate compartment of a dual-compartment dispensing apparatus. The compositions include the following components:

|  | Wt. % |
|---|---|
| COMPOSITION A | |
| Aqueous Composition | |
| Deionized Water | 77.0 |
| Ethyl Alcohol | 8.0 |
| Butylene Glycol | 6.0 |
| Triethanolamine | 4.0 |
| Dimethicone Copolyol | 4.0 |
| Eusolex 232 (sunscreen) | 0.5 |
| Methyl Cellulose | 0.5 |
| COMPOSITION B | |
| Anhydrous Composition | |
| Carbowax 200 | 82.0 |
| Ascorbic Acid (Vitamin C) | 5.0 |
| Ethyl Alcohol | 5.0 |
| Anhydrous Glycolic Acid | 3.0 |
| Isostearic Acid | 3.0 |
| Dimethicone | 2.0 |

EXAMPLE 3

An aqueous and an anhydrous composition according to the present invention is set forth below. Each of the compositions is charged to a respective separate compartment of a dual-compartment dispensing apparatus. The compositions include the following components:

|  | Wt. % |
|---|---|
| COMPOSITION A | |
| Aqueous Composition | |
| Deionized Water | 83.7 |
| Propylene Glycol | 8.0 |
| Isopropanol | 3.0 |
| 2-Amino-2-methylpropan-1-ol | 3.0 |
| Dimethicone Copolyol | 2.0 |
| Hydroxypropyl Methyl Cellulose | 0.3 |
| COMPOSITION B | |
| Anhydrous Composition | |
| Carbowax 400 | 83.0 |
| Ascorbic Acid (Vitamin C) | 5.0 |
| Glycerin | 5.0 |
| Anhydrous Lactic Acid | 3.0 |
| Linolenic Acid | 2.0 |
| Dimethicone Copolyol | 2.0 |

EXAMPLE 4

An aqueous and an anhydrous composition according to the present invention are set forth below. Each of the compositions is charged to a respective separate compartment of a dual-compartment dispensing apparatus. The compositions include the following components:

|  | Wt. % |
|---|---|
| COMPOSITION A | |
| Aqueous Composition | |
| Deionized Water | 80.7 |
| Propylene Glycol | 8.0 |
| Ethyl Alcohol | 6.5 |
| Triethanolamine | 4.0 |
| Eusolex 232 (sunscreen) | 0.5 |
| Sodium Carboxymethyl Cellulose | 0.3 |
| COMPOSITION B | |
| Anhydrous Composition | |
| Carbowax 200 | 76.0 |
| Ascorbic Acid (Vitamin C) | 10.0 |
| Ethyl Alcohol | 5.0 |
| Anhydrous Malic Acid | 3.0 |

-continued

| | Wt. % |
|---|---|
| Oleic Acid | 3.0 |
| Polyoxyethylene 15 Trimethylolpropane Isostearate | 3.0 |

EXAMPLE 5

An aqueous and an anhydrous composition according to the present invention are set forth below. Each of the compositions is charged to a respective separate compartment of a dual-compartment dispensing apparatus. The compositions include the following components:

| | Wt. % |
|---|---|
| COMPOSITION A | |
| Aqueous Composition | |
| Deionized Water | 83.0 |
| Ethyl Alcohol | 5.0 |
| Butylene Glycol | 5.0 |
| Ammonium Hydroxide | 4.0 |
| Dimethicone Copolyol | 2.5 |
| Methyl Cellulose | 0.5 |
| COMPOSITION B | |
| Anhydrous Composition | |
| Carbowax 400 | 80.9 |
| Isostearic Acid | 7.0 |
| Ascorbic Acid (Vitamin C) | 5.0 |
| Ethyl Alcohol | 5.0 |
| Polyoxyethylene 15 Trimethylolpropane Isostearate | 2.0 |
| Anhydrous Citric Acid | 0.1 |

EXAMPLE 6

A set of experiments were conducted to evaluate the effects of stearic versus isostearic acids on solution clarity when the aqueous and anhydrous compositions are mixed. These tests and their results are outlined in the Table below. Product A resulted in a white milky solution when components I and II were combined. By contrast, substitution of isostearic acid for stearic acid resulted in a clear solution. Absent the triethanolamine, the isostearic acid based Product C also formed a cloudy solution when components I and II were combined. From these experiments it is evident that the anhydrous composition requires a liquid organic acid such as isostearic acid and the aqueous composition requires an alkaline agent in order to provide a resultant clear solution.

TABLE I

| COMPONENT | PRODUCT (WT. %) | | |
|---|---|---|---|
| | 1 | 2 | 3 |
| I. Anhydrous Composition | | | |
| Carbowax 200 (Polyethylene Glycol) | 80 | 80 | 80 |
| Stearic Acid | 5 | — | — |
| Isostearic Acid | — | 5 | 5 |
| II. Aqueous Composition | | | |
| Deionized Water | 14 | 14 | 15 |
| Triethanolamine | 1 | 1 | — |
| Physical Appearance I & II Combined | Milky Solution | Clear Solution | Cloudy Solution |

The foregoing description and examples illustrate selected embodiments of the present invention and in light thereof variations and modifications will be suggested to one skilled in the art, all of which are in the spirit and purview of this invention.

What is claimed is:

1. A cosmetic product formed as a dual-compartment dispenser, wherein a first and second substance each of which are transparent are stored apart from one another in separate compartments of the dual-compartment dispenser, wherein:

(i) the first substance comprises from 0.01 to 50% by weight thereof of a liquid organic acid selected from the group, consisting of isostearic acid oleic acid, linolenic acid, linoleic acid and combinations thereof, and from 0.01 to 99% by weight thereof of a pharmaceutically acceptable carrier; and (ii) the second substance comprises an alkaline agent selected from the group consisting of ammonia, triethylamine, triethanolamine, diethanolamine, tetra(hydroxypropyl) diamine, 2-amino-2-methylpropan-1-ol, 2-amino-2-ethyl-1-3-propanediol and 2-amino-2-hydroxymethyl-1,3-propanediol present in an amount from about; 0.5 to about 30% by weight to neutralize the liquid organic acid to thereby form a surfactant active material, and wherein combination of the first and second substances provides a clear resultant mixture.

2. The cosmetic product according to claim 1 wherein the organic acid is present in an amount of from about 0.5 to about 25% by weight.

3. The cosmetic product according to claim 1 wherein the alkaline agent is triethanolamine.

4. The cosmetic product according to claim 1 wherein the liquid organic acid is isostearic acid.

* * * * *